US 6,719,868 B1
Apr. 13, 2004

(54) METHODS FOR FABRICATING MICROFLUIDIC STRUCTURES

(75) Inventors: Olivier J. A. Schueller, Somerville, MA (US); David C. Duffy, Cambridge, MA (US); John A. Rogers, New Providence, NJ (US); Scott T. Brittain, Southside, AL (US); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/425,787

(22) Filed: Oct. 22, 1999

Related U.S. Application Data

(63) Continuation-in-part of application No. 09/274,372, filed on Mar. 23, 1999, now abandoned.
(60) Provisional application No. 60/078,984, filed on Mar. 23, 1998.

(51) Int. Cl.[7] .............................................. B32B 31/12
(52) U.S. Cl. ............................... 156/272.6; 156/273.3; 156/292
(58) Field of Search ........................... 156/272.6, 273.3, 156/292, 306.3

(56) References Cited

U.S. PATENT DOCUMENTS 5,647,939 A  *  7/1997  Gee et al. ................. 156/272.6
5,932,799 A     8/1999  Moles
5,942,443 A  *  8/1999  Parce et al. ................. 436/514

OTHER PUBLICATIONS

Freemantle, Michael, "Chemical analysis and synthesis on microchips promise a variety of potential benefits,"Chemical & Engineering News, Feb. 22, 1999, pp. 27–36.

Takei, Hiroyuki, et al., "Spatial light modulation based on photoinduced change in the complex refractive index of bacteiorhodopsin," Applied Optics, Apr. 10, 1996, vol. 35, No. 11, pp. 1848–1854, Optical Society of America.

Jaecklin, V.P., et al., "Line–addressable torsional micromirrors for light modulator arrays," Sensors and Actuators A, 1994, pp. 324–329.

Buydens, L., et al., "Amplitude modulation and beam–steering properties of active binary phase gratings with reconfigurable absorption areas,"Jul. 20, 1994, Applied Optics, vol. 33, No. 21, pp. 4792–4800.

Solgaard, O., et al., "Deformable grating optical modulator," Optics Letters, May 1, 1992, vol. 17, No. 9, pp. 688–690, Optical Society of America.

Holtz, John, et al., "Polymerized colloidal crystal hydrogel films as intelligent chemical sensing materials,"Nature, Oct. 23, 1997, vol. 389, pp. 829–832.

Subacius, D., et al., "Switchable diffractive cholesteric gratings,"Applied Physics Letters, Sep. 8, 1997, vol. 71, No. 10, pp. 1350–1352, American Institute of Physics.

Duffy, David C., et al., "Rapid Prototyping of Microfluidic Systems in Poly(dimethysiloxane),"Analytical Chemistry, Dec. 1, 1998, vol. 70, No. 23, pp. 4974–4984, American Chemical Society.

(List continued on next page.)

Primary Examiner—Jeff H. Aftergut
Assistant Examiner—John T. Haran
(74) Attorney, Agent, or Firm—Wolf, Greenfield & Sacks, P.C.

(57) ABSTRACT

A system is provided for positioning separate portions of a sample in elongate, parallel channels of a sample chamber and to irradiate a sample in the chamber to create a diffraction pattern where the sample and chamber differ in refractive index. The system also can measure absorption of electromagnetic radiation by a sample in the chamber, and can measure the absorption simultaneously with measurement of diffraction by the sample.

27 Claims, 9 Drawing Sheets

OTHER PUBLICATIONS

Delamarche, Emmanuel, et al., "Microfluidic Networks for Chemical Patterning of Substrates: Design and Application to Bioassays," J. Am. Chem. Soc., Jan. 9, 1998, vol. 120, No. 3, pp. 500–508, American Chemical Society.

Woolley, Adam T., et al., "High–Speed DNA Genotyping using Microfabricated Capillary Array Electrophoresis Chips,"Analytical Chemistry, Jun. 1, 1997, vol. 69, No. 11, pp. 2181–2186.

* cited by examiner

Fig. 2A $$\delta\varphi = \frac{2\pi}{\lambda} d\Delta n$$

METHODS FOR FABRICATING MICROFLUIDIC STRUCTURES

This application is a continuation-in-part of application Ser. No. 09/274,372, filed Mar. 23, 1999, entitled Optical Modular/Detector Based on Reconfigurable Diffraction Grating, now abandoned, which claims the benefit Under Title 35 U.S.C. §119(e) of application Ser. No. 60/078,984 filed Mar. 23, 1998, both incorporated herein by reference.

FIELD OF THE INVENTION

The present invention relates generally to optical devices and, more particularly, to a microfluidic device defined by a plurality of parallel, elongate channels for containing a sample and optical apparatus for irradiating a sample in the channels and measuring absorption of the sample and diffraction of electromagnetic radiation by the system for sensor and modulation applications.

RIGHTS IN THE INVENTION

The invention described herein was supported at least in part by the Defense Advanced Research Project Agency (DARPA) and by the National Science Foundation (NSF) under award ECS-9729405. The government has certain rights in the invention.

BACKGROUND OF THE INVENTION

Devices for spatial light modulation based on liquid crystals, colloidal crystal hydrogels, materials showing photochromic and photoelastic effects, and micromachined structures are known. Some of these devices operate by exploiting differences in phase or absorption of electromagnetic radiation.

Differences in phase of electromagnetic radiation can be produced by varying a path that the radiation follows, for example by passage of the radiation through media of differing refractive index. Phase differences of light have been exploited for a variety of uses including sensors, apparatus for photolithography, optical displays, optical communication, fiber optic carriers, and the like.

Absorption of material by electromagnetic radiation is determied routinely. Absorption of light by fluid samples typically is determined by measuring absorption of light through an empty sample chamber, then measuring absorption of the same light through the same chamber filled with a sample, and comparing the two. A source of electromagnetic radiation is positioned on a first side of the chamber and a detector is positioned on the opposite side to detect radiation passing through the chamber, both filled and unfilled. These procedures are carried out with so-called absorption spectrometers which can determine absorption of a sample over a range of electromagnetic radiation frequencies.

Solgaard, et al., in "Deformable Grating Optical Modulator", *Optics Letters* 17, 9 (1992) describe a deformable light grating modulator based on electrically controlling the amplitude of a micromachined phase grating. The described structure includes silicon nitride beams suspended above a substrate. With no voltage applied between the substrate and the individual beams, the total path length difference for light reflected from the beams and from the substrate equals the wavelength of the incoming light. Reflections from the beams and from the substrate add in phase, and the grating reflects the light as a flat mirror. When a voltage is applied between the beams and the substrate, electrostatic force pulls the beams down. The total path length difference for the light reflected from the beams and from the substrate is now ½ of the wavelength, and the reflections interfere destructively, causing light to be diffracted. Solgaard, et al., state that ease of integration is expected to make deformable mirror modulators strong competitors with liquid crystal and electro-optic spacial light modulators in display technologies and for optical signal processing.

Delamarche, et al., "Microfluidic Networks for Chemical Patterning of Substrates: Design and Application to Bioassays," *J. Am. Chem. Soc.*, 1998, 120, 500–508, describe a microfluidic network useful for the small-scale patterned delivery of reactants to surfaces using the elastomer poly(dimethylsiloxane) as at least a portion of the channels. Woolley, et al., in "High-Speed DNA Genotyping Using Microfabricated Capillary Array Electrophoresis Chips," *Analytical Chemistry*, 69:11, Jun. 1, 1997, describe flowing a fluid through multiple channels and measuring optical characteristics of the fluid.

As mentioned above, measurement of properties of fluid samples in sample chambers is carried out routinely. There are many uses for systems that cause fluid to flow through channels, including very small channels. In an article entitled "Downsizing Chemistry," *Chemical & Engineering News*, Feb. 22, 1999, 27–36, a variety of systems are described for analyzing very small amounts of samples and reagents on chemical "chips" that include very small fluid channels and small reaction/analysis chambers. Small-scale systems are currently being developed for genetic analysis, clinical diagnostics, drug screening, and environmental monitoring. Such small-scale systems are commonly referred to as Microscale Total Analysis Systems (see, for example, Kricka, L. J.; Wilding, P. Micromechanics and Nanotechnology, in *Handbook of Clinical Automation, Robotics and Optimization*, Kost, G. J., Welsh, J., Eds., John Wiley and Sons, New York, 1996, p. 45; van den Berg, A., Bergveld, P., Eds., *Micro Total Analysis Systems*, Kluwer Academic Publishers, London, 1995; Manz, A., Becker, H., Eds. *Microsystem Technology in Chemistry and Life Sciences*, Springer-Verlag, Berlin, Germany, 1998; Manz, A., Harrison, D. J., Verpoorte, E., Wildmer, H. M. *Adv. Chromatogr.*, 1993, 33, 1; Kricka, L. J., Wilding, P. *Pure Appl. Chem.*, 1996, 68, 1831). Microscale Total Analysis Systems must be able to handle liquid or gas samples at very small scale, and must be compatible with chip-based substrates. Microfluidics, the behavior of fluid flow in very small-scale systems, therefore is central to the development of these systems.

Miniaturized capillary electrophoresis systems are known. Capillary electrophoresis is a separation technique that, conventionally, is typically carried out in fused silica capillaries. Capillary electrophoresis within polymer channels also is known. For a discussion of miniaturized capillary electrophoresis techniques, see Duffy et al., "Rapid Prototyping of Microfluidic Systems in Poly (dimethylsiloxane)," *Analytical Chemistry*, 70, 23, 4974–4984 (Dec. 1, 1998), and references therein.

Electroosmotic flow is a known technique for urging the flow of fluid within a channel by applying electric fields along the channels. Electroosmotic flow typically is carried out within glass channels in which it is relatively easy to create a negatively-charged interior channel surface to support electroosmotic flow.

Microfluidic systems based upon poly(dimethylsiloxane) are known. See Duffy, et al., referenced above, and references therein.

While the above and other reports describe in many cases useful optical modulators and sensors, and useful microfluidic systems, a need exists for simplified, inexpensive devices that can serve as effective modulators and/or can provide significant information when used as a sensor and microfluidic systems that can be used in these and other techniques. It is an object of the invention to provide such devices.

SUMMARY OF THE INVENTION

The present invention provides systems and methods for optical modulation and sensing. Some of these aspects and methods are described in the accompanying claims.

A device of the invention can be a diffraction grating defined by essentially parallel lines. But the device is not limited to a diffraction grating with evenly spaced, parallel lines. By changing the width and spacing of the microchannels more complex light patterns can be made, e.g. a variety of patterns defined by microchannels that change the spatial distribution of light passing through the device through diffraction effects, through constructive and destructive interference of light passing through different regions of the device, such as a Fresnel lens that focuses light using a planar array of channels.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

The present invention provides, in one aspect, a sensor that can simultaneously determine refractive index and absorption of a sample.

Figure 2:
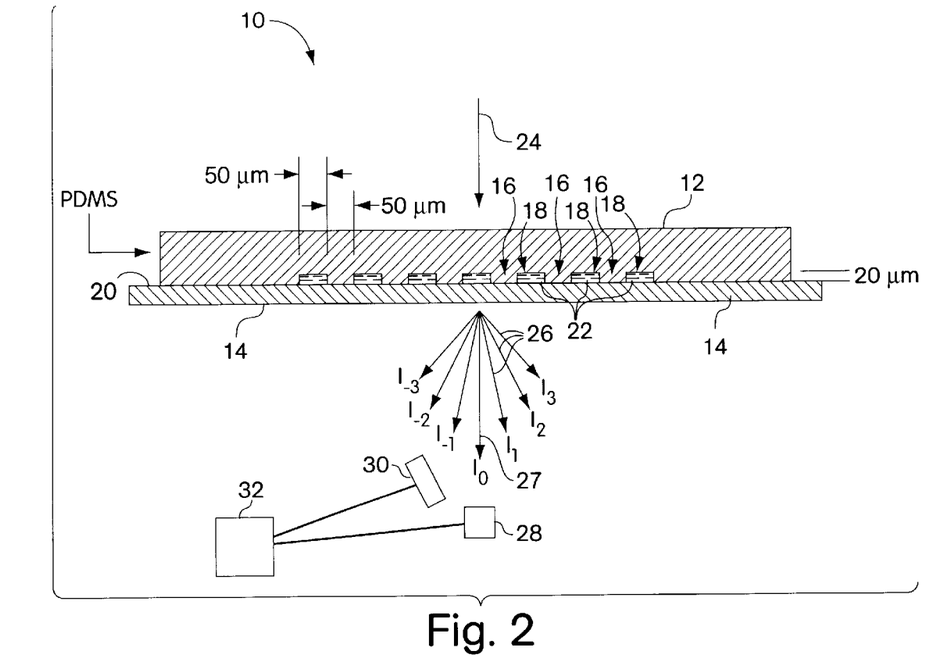
FIG. 2 is a schematic cross-section of a microfluidic device of the invention that can function as a diffraction grating or absorption device, and is a cross-section through lines 2—2 of FIG. 2A.

Referring to FIG. 2, a sensor system 10 is illustrated schematically including a first component 12 and a second component 14. First component 12 has a first surface 14 defining a plurality of protrusions 16 and indentations 18. Outward facing surfaces of protrusions 16 contact a surface 20 of second component 14. This defines a plurality of channels 22 each defined by indentations 18 and portions of surface 20 in register with these indentations, which together define a sample chamber. Component 12 is shown in FIG. 2 in end view, or cross-section. The channels 22 are elongate channels that extend into and out of the page. Components 12 and 14 are part of system 10 which defines a sample chamber including the plurality of channels 22. Components 12 and 20 are at least partially transparent to incident electromagnetic radiation used in the techniques described below, and preferably is essentially completely transparent to such radiation.

If a sample contained within channels 22 has a refractive index essentially identical to that of component 12, then when an incident beam of the electromagnetic radiation 24 impinges upon a sample within channels 22, the beam passes through un-diffracted. If a sample in channels 22 has a refractive index different from the material of component 12, then incident beam 24 is diffracted and emerges as diffracted beams 26. A detector can be positioned to detect whether diffraction occurs, and the extent to which diffraction occurs. Where diffraction does not occur, all of the incident beam 24 emerges as beam 27. That is, the beam is not diffracted. But where diffraction occurs, some of incident beam 24 is diffracted as diffracted beams 26 (1, 2, 3, −1, −2, and −3). Thus, a detector positioned to detect the existence and intensity of any of these diffracted beams 1, 2, 3, −1, −2, and −3 can determine the existence and degree of diffraction. The optical properties (index of refraction; absorption) of the sample filling the channels dictate the appearance of the diffraction pattern produced by the grating. The period of the grating determines the angular position of the diffracted beams, while the thickness of the channels and the optical properties of the fluid determine their relative intensities.

The Fraunhofer (far-field) diffraction pattern can be calculated by Fourier transformation of the transmission function of the grating. The transmission function, $\tau(x)$, of the microfluidic diffraction grating is given by Eq. 1, where $\delta\phi$ is the difference in the phase of light that passes through the microchannels and the light that passes through PDMS only, T is the transmittance of the fluid in the microchannels, w is the width of the microchannels, and p is the period of the grating:

$$\tau(x) = \begin{cases} \sqrt{T}\, e^{i\delta\varphi} & kp < x < kp + w \quad k \text{ integer} \\ 1 & \text{otherwise} \end{cases} \quad (1)$$

Eq. 1 indicates that the transmission function and hence the diffraction pattern can be changed by either modulating the phase or changing the amplitude of the light that passes through the microfluidic channels. The modulation of the phase is determined by the profile of the index of refraction of the grating. The phase difference is given by Eq. 2, where $\lambda$ is the wavelength of the light, d is the depth of the channels, and $\Delta n = n_p - n_f$, i.e., the difference between the index of refraction of PDMS ($n_p \sim 1.41$) and that of the fluid filling the channels ($n_f$):

$$\delta\phi = \frac{2\pi}{\lambda} d \Delta n \quad (2)$$

Figure 4:
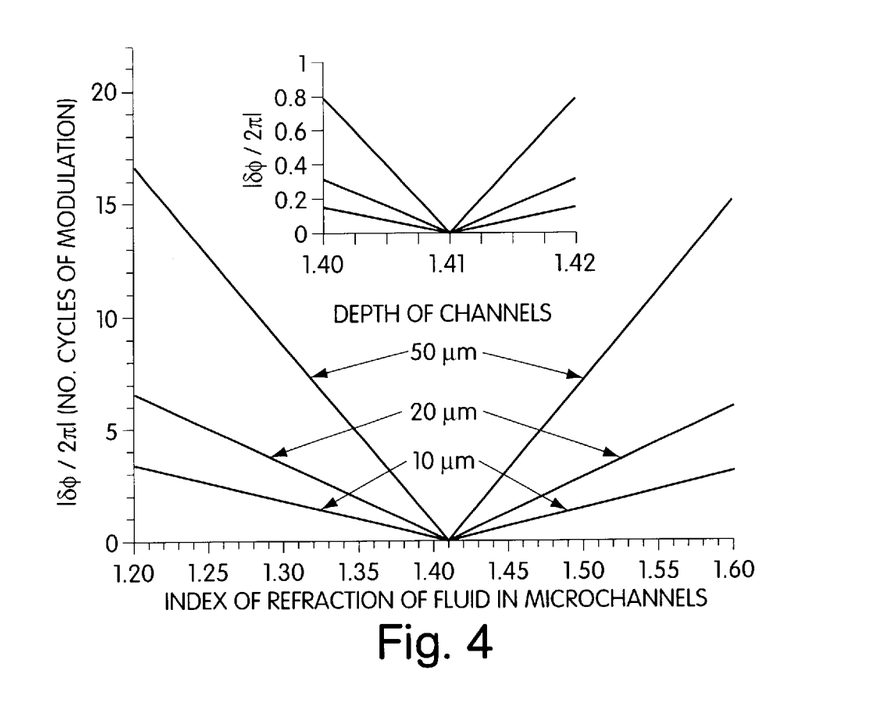
FIG. 4 illustrates modulation of phase difference as a function of index of refraction of a fluid in a device of FIGS. 1–3 for different channel dimensions.

By filling the channels with fluids that have different indices of refraction, the phase of a given microfluidic device can therefore be modulated. For examples: if empty channels are filled with water, the phase shift $\Delta\Phi$ between the two states (filled vs. empty) is $\delta\Phi_{filled} - \delta\Phi_{empty}$: this difference is equal to $21\pi$ or about 10 modulation cycles at 633 nm for 20-$\mu$m thick channels; if the index of refraction of the fluid filling the channels matches that of PDMS, then the phase will not be modulated and the device will transmit light without diffracting it. Eq. 2 shows that the modulation of phase is effected by the thickness of the microfluidic channels: to illustrate this effect, $|\delta\Phi/2\pi|$ is plotted as a function of the index of refraction of the fluid filling channels for three different channel thicknesses in FIG. 4. Each unit on the y-axis of this plot represents one cycle in the modulation of the phase of the microfluidic diffraction grating as the index of refraction of the fluid changes. FIG. 4 shows that diffraction gratings with thicker channels will be more sensitive than thinner channels to small changes in the index of refraction of a fluid. Specifically, FIG. 4 shows modulation of the phase difference, $\delta\Phi$, as a function of the index of refraction of the fluid for diffraction gratings with channels that are 10, 20, and 50 $\mu$m thick at 633 nm: a change in $\delta\Phi$ of $2\pi$ represents 1 cycle of modulation. When the index of refraction of the fluid matches that of PDMS ($n_p \sim 1.41$), the device is completely transparent and no diffraction takes place. The sensitivity of the device to changes in index of refraction of the fluid increases with the thickness of the microchannels. The inset shows how the phase difference varies with small changes in index of refraction.

If the channels of a microfluidic diffraction grating are filled with a fluid that absorbs light, then the amplitude as well as the phase of the light passing through the microchannels is effected. Eq. 1 indicates that, in this case, the intensities of the diffracted beams will depend on both the difference in phase and the amount of light that is absorbed by the fluid. For example, a difference in phase of $\pi$ results in total extinction of the 0th order diffracted spot only when the beams that interfere destructively have the same amplitude; if the amplitude of the light passing through the fluid is changed due to absorption, then there will not be complete destructive interference and the intensity of the 0th order diffracted spot will be non-zero even though the difference is phase is $\pi$.

The influence of the geometry of the microchannels filled with an absorbing liquid on the transmittance, T, is illustrated by the Beer-Lambert law (Eq. 3) that describes the effect on T of an absorber at low concentrations. In Eq. 3, $I_0$ and I are the intensities of the incident and transmitted beams, respectively, $\epsilon$ is the molar absorption coefficient, [C] is the concentration of absorbing species in the solution, and d is the thickness of the microchannels:

$$\frac{I}{I_0} = T = 10^{-\epsilon[C]d} \quad (3)$$

Figure 5:
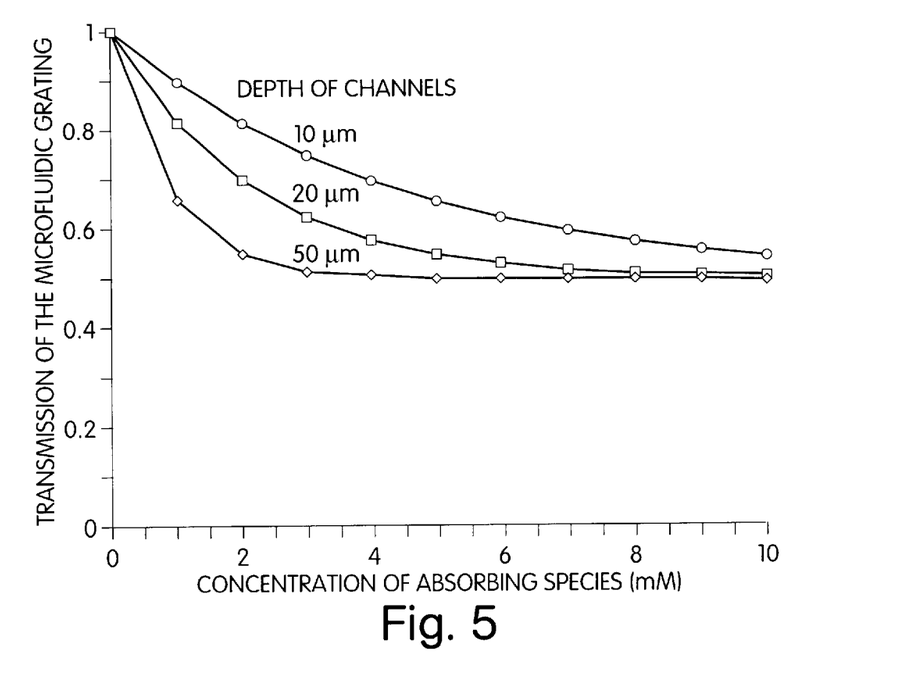
FIG. 5 shows variation of transmission coefficient of the device of FIGS. 1–3 as a function of concentration of an arbitrary absorbing species.

Eq. 3 shows that the transmittance decreases exponentially as $\epsilon$, [C], or d increases. FIG. 5 illustrates the variation of the transmission of microfluidic diffraction gratings as a function of concentration of an absorbing fluid and the thickness of the microchannels. Small changes in concentration (at low values of concentration) have a strong effect on the transmission of the device, and hence on the diffraction pattern, for thick microchannels. FIG. 5 shows variation of the transmission coefficient of the microfluidic diffraction grating, from values of T (the transmittance of the channels) calculated using the Beer-Lambert law (Eq. 3), as a function of the concentration of an arbitrary absorbing species, assumed to have $\epsilon \sim 10^5$ $M^{-1}cm^{-1}$, in the microchannels. As the thickness of the microchannels increases, the transmission decreases: Eq. 1 indicates that this decrease will change the relative intensity distribution of the diffraction pattern.

Figure 6:
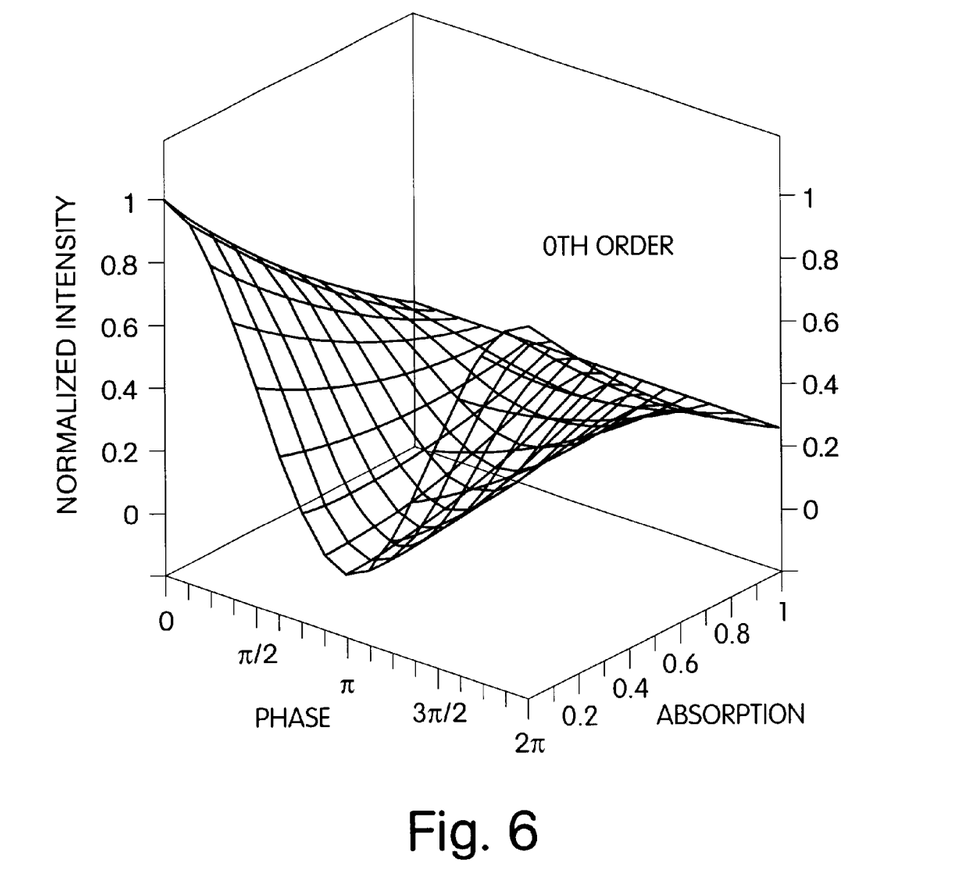
FIGS. 6 and 7 show variation in the intensities of 0th and 1st order diffracted beams as a function of phase and absorption of the microchannels of the device of FIGS. 1–3 filled with fluid.
Figure 7:
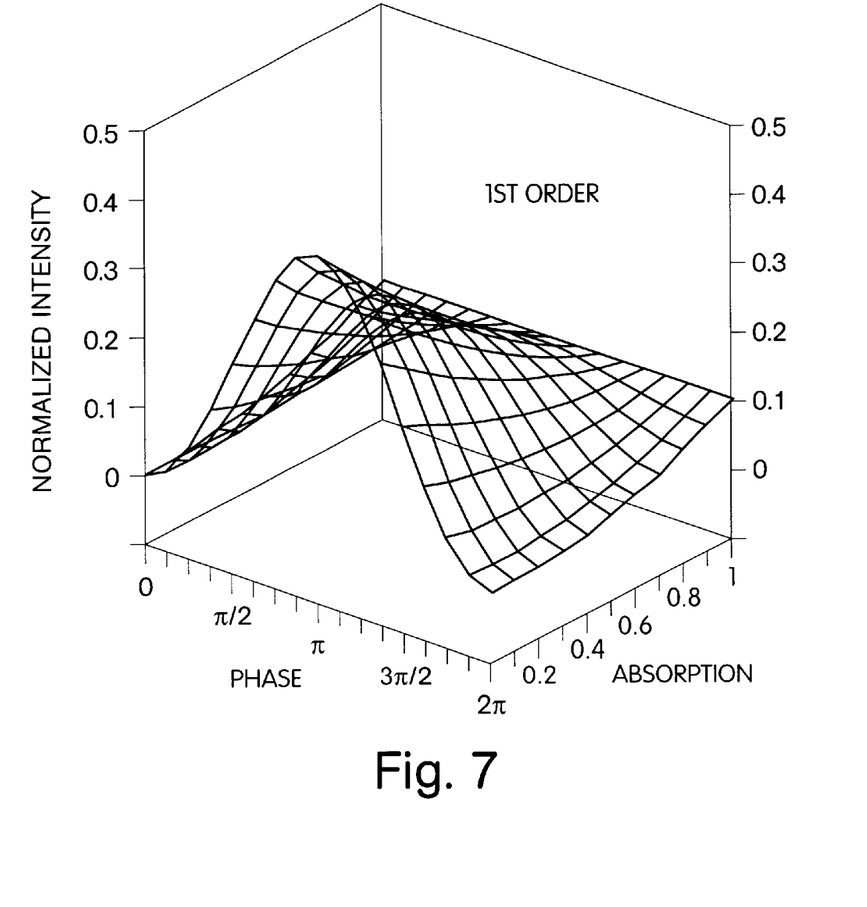

In general, the microfluidic diffraction grating will not operate as a pure phase or amplitude grating: the variation in the intensities of the diffracted beams will be determined by changes in both $\delta\Phi$ and T. We determined numerical solutions of the Fourier transformation of Eq. 1 to model the behavior of the gratings as a function of the optical properties of the fluid. The variations in the intensities of the 0th and 1st orders diffracted beams as a function of both phase and absorption are plotted in FIGS. 6 and 7. The intensity of the 0th (1st) order beam is maximum (minimum) when the depth of modulation of the phase is 0 or $2\pi$, and minimum (maximum) when the depth of modulation of the phase is $\pi$. If the index of refraction of a non-absorbing fluid filling the channels varies over a sufficiently wide range so that the resulting shift in phase is $\sim\pi$, the optical response of a microfluidic diffraction grating is switched between two extremes: i.e., from a state in which the 0th order beam is fully illuminated to one in which it is fully extinct. If the absorption of the fluid in the microchannels changes, the relative intensities of the various diffracted orders change: for example, the maximum contrast between 9th and 1st order diffracted beams decreases as the absorption increases. Specifically, FIGS. 6 and 7 show variation in the intensities of the 0th (6) and 1st (7) order diffracted beams as a function of the phase and absorption $(1-\sqrt{T})$ of the microchannels filled with fluid. These plots were generated by Fourier transformation of Eq. 1.

The device illustrated schematically in FIG. 2 is useful in a variety of situations. For example, system 10 can be used to determine the existence or concentration of an analyte carried in a fluid where the analyte changes the refractive index of the fluid. If a fluid carrier is passed through channels 22, and the fluid contains a varying degree of an analyte that changes the refractive index of the carrier fluid, then this difference in refractive index will result in a change in intensity of diffracted beams 26 relative to un-diffracted beam 27 as the concentration of the analyte in the fluid passing through channels 22 changes (i.e. as the fluid passes through the channels).

If an analyte carried by fluid 22 changes the absorption characteristics of the fluid, but the fluid and analyte together have the same refractive index of component 12, then only un-diffracted beam 27 emerges upon exposure of the system to electromagnetic radiation, but the intensity of beam 27 changes with the concentration of the analyte.

The present invention, in one aspect, involves the recognition that a change in absorption, and refractive index, of a sample passing through channels 22 can be determined simultaneously. This can be accomplished by providing an electromagnetic radiation detector (photodetector) 28 positioned in line with un-diffracted beam 27, and a similar detector 30 positioned in line with any of the diffracted beams 26, for example in line with beam −1 as illustrated. These can be connected to a processor 32 constructed and arranged to measure the intensity of electromagnetic radiation striking detector 28, and the intensity of electromagnetic radiation striking detector 30. Where the refractive index of fluid passing through channels 22 of system 10 changes, this can be determined at processor 32 by determining a change in the ratio of intensity of electromagnetic radiation striking detectors 28 and 30, respectively. Where the absorption of fluid passing through channels 22 changes, this can be determined at processor 32 by determining a change in total electromagnetic radiation striking detectors 28 and 30, combined. Thus, refractive index and absorption of fluid passing through channels 22 can be determined, simultaneously, as can any change in refractive index or absorption.

Thus, a first diffraction pattern can be established with system 10 resulting from interaction of electromagnetic radiation 24 with the system including separated portions of a first sample residing in adjacent channels 22. The portions are isolated from each other and no electromagnetic radiation interacts with the sample between the separated portions. The first sample can be changed to a second sample, i.e., by urging a fluid carrier through channels 22. In this arrangement the first sample is defined by portions of fluid in channels 22 in line with incident electromagnetic radiation beam 24, and the second sample defines a second portion of the sample in channels 22 in line with beam 24 after the sample moves within the channels. When the fluid moves within the channels, and the first sample is changed to the second sample, the difference between a first and second diffraction pattern can be determined by determining the difference in ratio of electromagnetic radiation striking detectors 28 and 30, respectively.

Figure 2A:
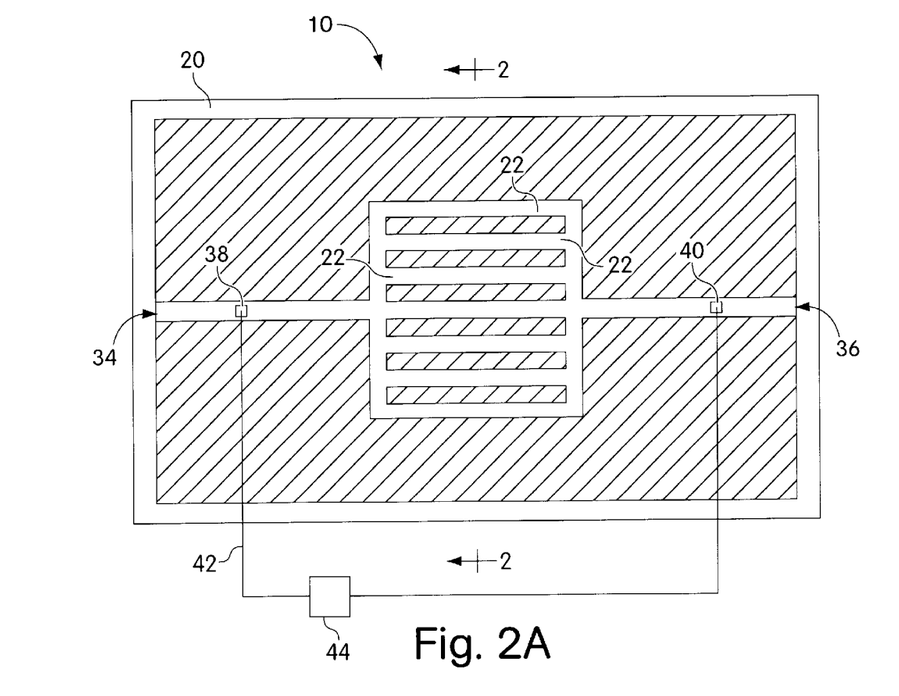
FIG. 2A illustrates schematically a top view of a microfluidic device of the invention in cross-section.

FIG. 2A illustrates a top view of system 10 where FIG. 2 is a cross-section taken through lines 2—2 of FIG. 2A. In FIG. 2A a sample inlet channel 34 and a sample outlet channel 36 are illustrated which each fluidly connect to each of channels 22 and are constructed to deliver fluid to and remove fluid from channels 22. It is emphasized that the system as illustrated in FIG. 2 is schematic only. In preferred embodiments, fluid is delivered to each of channels 22 collaterally. That is, if fluid delivered by channel 34 increases in concentration of a particular analyte at a particular rate, then system 10 should be constructed, in terms of fluid dynamics, to position fluid in each of channels 22 that is identical in concentration of the analyte at identical locations, axially, within each channel.

A pump can be provided to deliver fluid sample to and urge fluid sample through the sample chamber. The pump can be a physical pump, such as a pump that applies pressure to fluid delivered to inlet channel 34, or applies vacuum to fluid exiting via channel 36. A peristaltic-type pump also can be provided where component 12 is flexible or, especially, where component 12 is elastomeric. That is, a series of rollers can continuously engage component 12 and compress the component downwardly, decreasing the cross-section of delivery channel 34 or exit channel 36, and the rollers can continuously be urged in the direction of delivery or removal to provide continuous flow through the channels.

Alternatively, an electroosmotic pump or pumps can be provided. In one embodiment this is represented by electrodes 38 and 40 provided in inlet channel 34 and exit channel 36, respectively, each addressed by electrical system circuitry 42 including an electric power source 44. Alternatively, a plurality of electrodes (not shown) can be provided in each of channels 22 to create electroosmotic pressure. In each case electrodes can be fabricated in component 20 via standard microfabrication techniques. That is, component 20 can be a chip, covered by component 12 which is positioned to provide channels in register with electrodes.

System 10 can be created in any way that provides a sample chamber that can provide a sample in separate, isolated portions such that electromagnetic radiation interaction with the system can cause diffraction, and such that absorption of the sample can be measured. That is, the system can include a one-piece container including a plurality of separate, elongate, essentially parallel channels, or component system as illustrated. In the system illustrated, components 20 and 12 can be made of any materials that are at least somewhat transparent to the electromagnetic radiation. Materials such as glass, quartz and polymers are contemplated. It is important only that a seal be created between outward-facing surfaces of protrusions 16 and portions of surface 20 in register therewith to allow fluid to be contained within samples 22. Components 12 and 20 can be adhered to each other via fluid-resistant adhesive, or the like.

In one set of preferred embodiments component 12 is a polymeric article, preferably an elastomeric article. One technique for fabrication of article 12 involves casting a polymeric article 12 on a contoured surface created via photolithography including a plurality of protrusions complementary to indentations 18 created in article 12. Contact-mode photolithography for this purpose can be carried out and as described in U.S. Pat. No. 5,512,131 of Kumar, et al., International patent publication number WO 96/29629 of Whitesides, et al., published Jun. 2, 1996, U.S. patent application Ser. No. 08/676,951, field Jul. 8, 1996 which is co-pending and commonly-owned, and co-pending, commonly-owned U.S. patent application Ser. Nos. 08/853,050 (Rogers, et al., filed May 8, 1997) and 08/873,191 (Qin, et al., filed Jun. 11, 1997, each incorporated herein by reference. In one technique a substrate is coated on one surface with a film of photoresist. Via standard photolithographic techniques, a pattern is created in the film of photoresist, the pattern corresponding the desired patterns of indentations 18. Transparent, elastomeric article 12 then is cast on the surface defined by the substrate and pattern of photoresist.

Component 12 can be cast from any precursor that, when solidified, will create an article that is transparent or semi-transparent to electromagnetic radiation of interest, a contoured surface that is conformable and/or includes indentations. "Transparent" or "semi-transparent" means that the article is sufficiently transparent to radiation to render the article useful for sensor or actuator techniques.

In one embodiment, component 12 is cast from a polymeric precursor having linear or branched backbones that are cross linked or non-cross linked, depending upon the particular polymer and degree of formability desired. A variety of elastomeric materials are suitable, especially polymers of the general classes of silicone polymers, epoxy polymers, and acrylate polymers. Epoxy polymers are characterized by the presence of a three-member cyclic ether group commonly referred to as an epoxy group, 1,2-epoxide, or oxirane. For example, diglycidyl ethers of bisphenol A may be used, in addition to compounds based on aromatic amine, triazine, and cycloaliphatic backbones. Another example includes the well-known Novolac polymers. Examples of silicone elastomers suitable for use as component 12 include those formed from precursors including the chlorosilanes such as methylchlorosilanes, ethylchlorosilanes, phenylchlorosilanes, and the like. A particularly preferred silicone elastomer is polydimethylsiloxane. Exemplary polydimethylsiloxane polymers include those sold under the trademark Sylgard by the Dow Chemical Company, Midland, Mich., and particularly Sylgard 182, Sylgard 184 and Sylgard 186.

While casting component 12 from a prepolymeric precursor on a surface patterned with photoresist is preferred, other techniques, such as casting component 12 from a surface patterned via machining, a surface patterned itself via casting on a photoresist-patterned surface, and the like are suitable. It is important only that component 12 be fabricated so as to include a plurality of protrusions 16 and indentations 18 that satisfy criteria that will become apparent.

In another embodiment component 12 is not flexible or elastomeric in its entirety, but the outward-facing surfaces of protrusions 16 are polymeric and preferably elastomeric and conformable to surface 20. In this way, if surface 20 includes imperfections in contour, component 12 and component 20 can easily form a seal between them.

Determining whether a particular material will be suitable for use in the invention can be readily determined by those of ordinary skill in the art. Conformability is routinely determined. Selection of material, in conjunction with selection of an electromagnetic radiation source, can be carried out by measuring an absorption spectrum of the material at the wavelength of the radiation source. If the article passes radiation produced by the source at a wavelength that is detectable (for sensor and display embodiments), then the material and radiation source are suitable for use in the invention.

The system of the invention defines a reconfigurable diffraction grating based on a microfluidic device. The array of channels 22 of FIGS. 1 and 2 and 2A can be fabricated to be approximately 50 microns wide and approximately 20 microns depth, although width and depth can be varied widely. Samples introduced into channels 22 can be fluids (gas, aqueous solutions, organic solutions, suspensions, and the like). The difference in index of refraction between the fluid in the array of microchannels and the structural elastomeric solid generates a difference in the phase of light passing through the device; absorption by the fluid changes the amplitude of the light. Both of these effects give rise to diffraction. Reconfiguration occurs when liquids with different indices of refraction and optical densities are pumped through the microchannels. Depths of modulation on the order of around 20 dB and switching times of around 50 ms are observed. The volume of liquid sampled by incident light in examples below is about 8 nL. The depth and width of microchannels 22 can be varied significantly between about 1 and 1000 microns.

When the diffraction pattern is measured, the absorption and the phase are determined. Although it is straightforward given the absorption and the depth of the channels to determine the concentration or the molar absorption coefficient, to interpret the phase is slightly more complex because everything is mod 2 pi (i.e. phase gratings that shift the phase by 2 pi look the same as those that shift the phase by 4 pi.) In many cases, monitoring changes in the phase will be sufficient because the changes are often very small compared to 2 pi. In other cases, however, it may be important to determine the index of refraction and not just the phase. There are several ways to determine the index of refraction from the diffraction pattern: (i) measure the diffraction at several laser wavelengths, or (ii) at a single laser wavelength, measure several gratings that have different channel depths, (iii) at a two wavelengths that are not integral multiples of one another, measure the diffraction pattern as a function of number of passes through the grating or (iv) some combination of (i), (ii) and (iii). In one embodiment a grating is constructed with channel depths that vary in a continuous way along the channels. Probing this type of structure at several (or many) points gives the dependence of the diffraction pattern on the channel depth, and yields the information required to determine the index accurately. One can achieve the necessary structure by the standard molding article 12 against an appropriate master. Or, one can form the structure by applying spatially varying force to a flexible article 12 that in its undeformed state has channel depths that do not vary along their length.

Devices described herein can be used as sensing elements in micrototal analysis systems and as actuators. The systems of the invention can be used in sensing, that is, real-time monitoring of the variation of index of refraction and absorption of a fluid (see Harrison, et al., *Sensors and Actuators* B-Chemical, 33 (1996) 105–109, incorporated herein by reference; O. Solgaard, et al., "Deformable grating optical modulator", *Opt. Lett.*, 17 (1992) 688–690; A. van den Berg, et al., "Micro Total Analysis Systems", Kluwer, Dordrecht, 1995; A. Manz, et al., "Microsystem technology in chemistry and life science", Springer, Berlin, 1998; E. M. J. Verpoorte, et al., "Three-dimensional micro flow manifolds for miniaturized chemical analysis systems", *J. Micromech. Microeng.*, 4 (1994) 246–256.

A sensor based on this device can be used to monitor the variations in the optical properties (index of refraction and absorption) of a fluid by measuring the intensities of diffracted beams. The switching time of this type of device (determined by the speed at which fluids can be pumped through the channels) is in the range of from about 1 to about 500 ms and allows it, for example, to be used in real-time monitoring of the evolution of a chemical reaction on a chip. Furthermore, the liquids in the channels can be pumped by electroosmosis as described above. This possibility makes the device compatible with many μTAS that use electric fields to pump liquids and to separate analytes. The detection of fluids by diffraction is sufficiently sensitive according to the invention to offer a simple and cheap alternative to detection that is inherently compatible with μTAS.

Also, these devices can be used in actuating, for example wavefront engineering, reconfigurable optical filters, and modulators (see, L. Buydens, et al., "Amplitude modulation and bea-steering properties of active binary phase gratings with reconfigurable absorption areas", *Appl. Opt.* 33 (1994) 4792–4800). Fluids with different optical properties can be pumped through the channels to modulate the diffraction of light. Complex modulations of diffraction can be achieved if the channels are addressed independently and filled with fluids with different optical properties. Microfluidic devices based on this concept can find applications in spatial light modulation or wavefront engineering, and can be used in beam-steering devices or phase arrays. This type of device is complementary to electrostatically-modulated diffraction gratings.

One aspect of the invention involves a technique for treating a surface to promote sealing of the surface to another surface or chemical modification of the surface in way that can promote fluid flow within a fluid channel defined in part by the surface. In a technique for promoting sealing, the invention involves sealing a first surface to a second surface where the first surface, the second surface, or both can be well-sealed to form a fluid-tight seal (a seal impermeable to fluids that are not destructive, i.e. do not dissolve or otherwise degrade, components joined to form the seal) in the absence of auxiliary adhesive. Auxiliary adhesive, in this context, means an agent, separate from components joined to form a seal, coated on one or both surfaces of the components at locations joined to form the seal. The technique involves, in one set of embodiments, pre-oxidizing the first, the second, or both surfaces prior to joining them. This is particularly useful when at least one surface is a polymeric surface. For example, a polymeric surface can be pre-oxidized and adjoined to a second surface, such as another polymer, glass or the like, that also is pre-oxidized, and the first and second surfaces can be joined and allowed to form a liquid-impermeable seal therebetween. Pre-oxidation can be carried out by exposing the surfaces to plasma and, where one or both surfaces expose silicon atoms, pre-oxidation of the surface can result in formation of siloxane bonds between the two surfaces when they are joined. For example, a silicon-containing polymer such as PDMS, when pre-oxidized via exposure to plasma, defines a conformable surface that can form a liquid-impermeable seal with another surface such as glass or PDMS via formation of siloxane bonds therebetween. It is particularly useful to select at least one component that is conformable (for example an elastomeric polymer) to form such a seal because in the absence of auxiliary adhesive, good surface contact between the two components greatly enhances good seal formation.

It is a feature of sealing techniques of the invention, involving pre-oxidation of polymeric or other surfaces via, for example, exposure to plasma and formation of siloxane bonds, that liquid-impermeable seals can be formed at or near room temperature. Specifically, a polymeric surface can be sealed to a second surface to form a liquid-impermeable seal, in the absence of auxiliary adhesive, at a temperature of between about 12° C. and about 34° C., more preferably from about 16° C. to about 27° C., more preferably still from about 18° C. to about 23° C. For a discussion of chemistry of plasma-induced sealing via formation of siloxane bonds, reference is made to Madou, "Fundamentals of Microfabrication," CRC Press, New York, pgs. 382–395, incorporated herein by reference.

Particularly relevant to fluid flow within channels, as described above, techniques of the invention advantageously can involve sealing outward-facing surfaces of protrusions 16 to surface 20 that does not require auxiliary adhesive. This technique can be applied to any of a variety of systems, not necessarily those systems described herein. This technique involves exposing outward-facing surfaces of protrusions 16 (optionally all of surface 14) to plasma, and then contacting first portions of the first surface (outward-facing surfaces of the protrusions) with the second surface while leaving a second portion of the first surface (indentation 18), intervening the first portions of the first surface, free of contact with the second surface. A seal is created in this manner that is impermeable to fluids that are not destructive (do not dissolve or otherwise degrade) components 12 or 20, in the absence of auxiliary adhesive.

Figure 1:
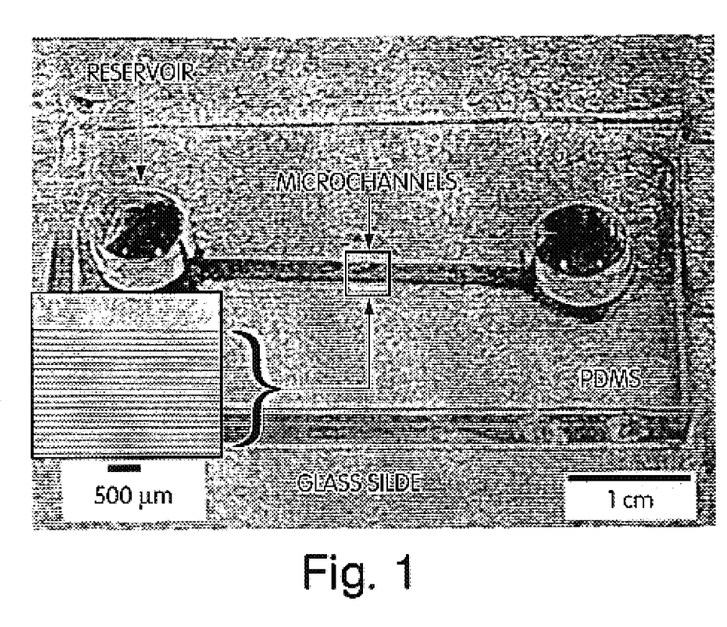
FIG. 1 is a photocopy of a slightly magnified microfluidic device of the invention, including a photocopy of a more highly-magnified section of channels of the device (inset)
Figure 3:
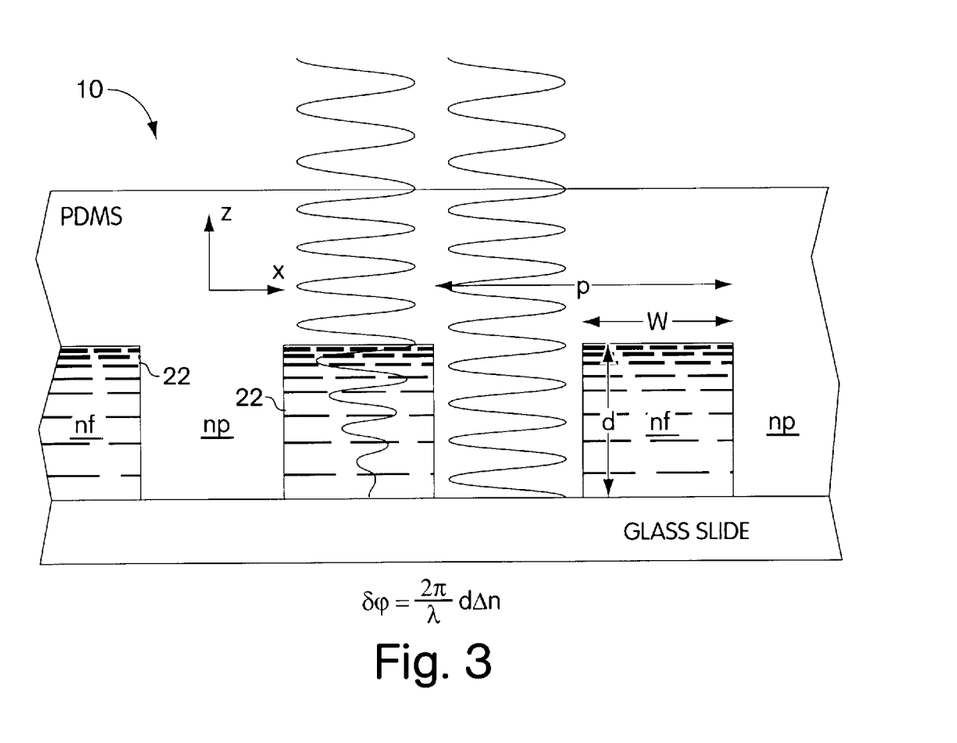
FIG. 3 illustrates schematically details of a grating of the invention for purposes of describing diffraction and absorption.

Plasma treatment to pre-oxidize a polymeric surface can be used according to another aspect of the invention involving inducing electroosmotic fluid flow in a channel where an interior surface of the channel is defined at least in part by the polymeric material. With reference to FIGS. 1–3, specifically FIG. 2 for purposes of this discussion, this can involve exposing surface 20 of component 14 to plasma, and exposing surface 14 of component 12 to plasma, where components 12 and 14 are made of material that will expose a charged surface upon exposure to plasma. For example, where surfaces 20 and 14 expose silicon atoms, e.g. where article 20 and 12 are glass or PDMS, exposure to plasma will result in exposed oxygen atoms that quickly become hydroxyl groups that carry a negative charge that can facilitate electroosmotic flow. Electroosmotic flow can be facilitated using electrical circuitry positioned to apply an electrical field along any one or all of channels 22 formed when articles 12 and 20 are joined to each other. Such electrical circuitry can readily be arranged by those of ordinary skill in the art and is not shown.

Another aspect of the invention involves chemical modification at surfaces promoted by a pretreatment step that can be the same step used to pre-oxidize a surface for bonding to another surface, or modification of a surface to facilitate electroosmotic flow. With reference to FIG. 2, exposure of surfaces 14 and 20 to plasma not only pre-oxidizes the surfaces such that bonding of surface 14 to surface 20 is promoted in the absence of auxiliary adhesive, but primes the interior surfaces of thus-formed channels 20 to chemical modification. Once channels 22 are defined by joining outward-facing surfaces of protrusions 16 to portions of surface 20 in register therewith, the interior surfaces of channels 22 can be modified to expose a predetermined chemical functionality. In one embodiment, the interior surfaces of channels 22 are modified by coating them with a chemical that bonds to the interior surface after the pretreatment step and that facilitates fluid flow within the channel. That is, fluid flow can be urged within the channels at a first fluid flow rate under conditions at which, had the pretreatment step not been carried out, the fluid would flow at a slower rate.

Figure 11:
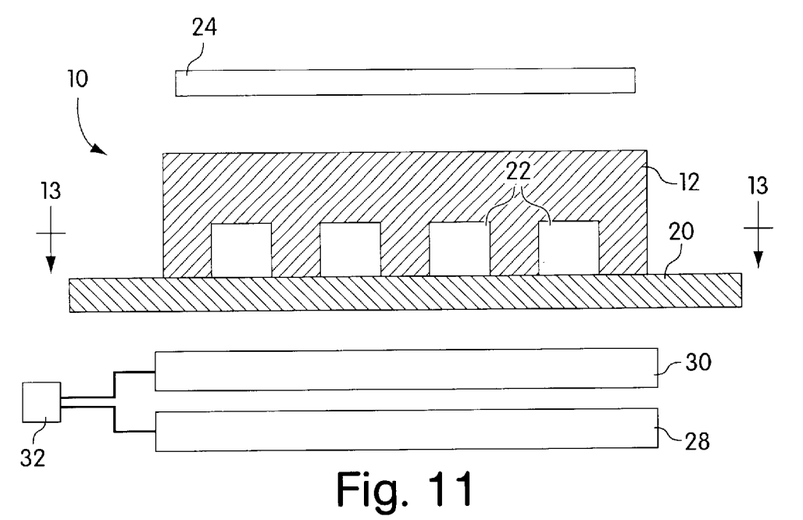
FIG. 11 is a cross-sectional schematic illustration of a device of the invention designed to measure both absorption and diffraction.
Figure 12:
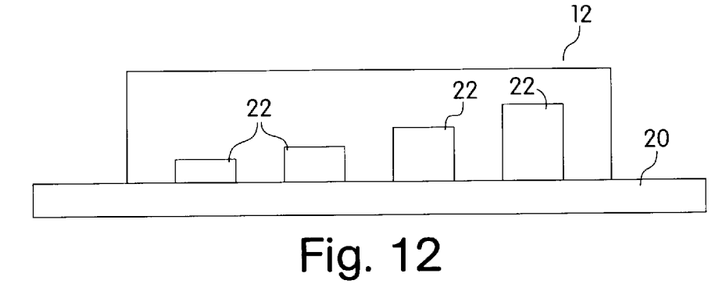
FIG. 12 is a schematic illustration of the effect of placing fluids of different refractive indices in different channels of the device of FIG. 10.

FIG. 11 illustrates schematically system 10 of the invention. Although not illustrated, each of channels 22 can be addressed by a different fluid source. This is routine to those of ordinary skill in the art. When fluids of different refractive index are passed through the different channels 22, the effect on passage of light, from source 24, can be essentially identical to a situation in which the depth of the channels varies, as illustrated in FIG. 12.

Figure 13:
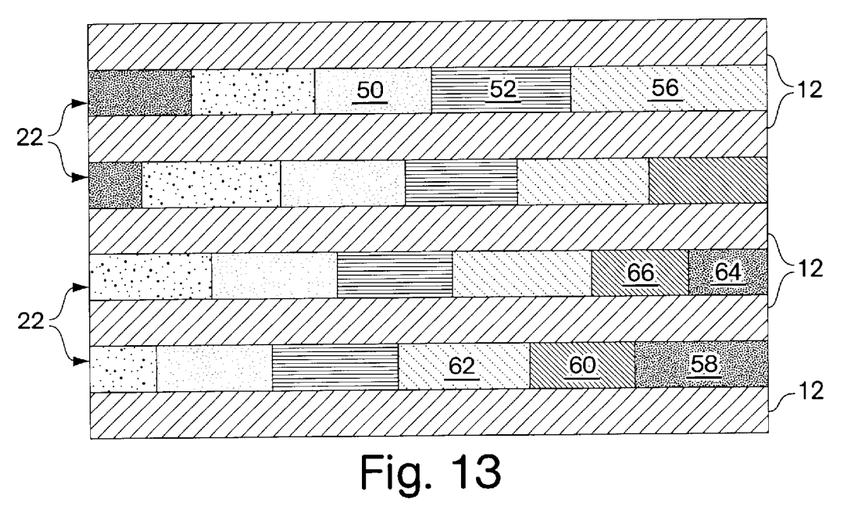
FIG. 13 is a top, cross-sectional, schematic illustration of the device of FIGS. 1–3 and 10 in which different fluids have been placed in different channels and the fluids differ as a function of axial position in each channel.

FIG. 13 illustrates system 10 through lines 13—13 of FIG. 11, in which channels 22 are not only filled with different fluids, but the content of the fluids changes axially along the channels. That is, sections of different fluid samples can be injected into each channel as desired. This creates "blocks" 50, 52, 56, 58, 60, 62, 64, 66, etc., that can be positioned as desired in any channel and at any position axially in the desired channel. This technique is best carried out using plugged-flow electroosmotic pressure to urge flow in the channels as described above. For example, a carrier channel can be provided with branches that supply samples. Electrodes can be provided to urge samples into the carrier channel in appropriate sequence, and a control system can be provided to activate the electrodes when required. The system of FIG. 13, when exposed to electromagnetic radiation, produces a two-dimensionally variant pattern. That is, different samples having different refractive indices and/or absorption characteristics can be positioned as desired to generate a display (diffraction pattern, etc.), to serve as a detector, etc.

EXAMPLES

Elastomeric diffraction gratings were prepared by casting PDMS prepolymer (Sylgard 184, Dow Corning) onto a patterned photoresist surface relief (the master) generated by photolithography. A. Kumar and G. M. Whitesides, Features of gold having micrometer to centimeter dimensions can be formed through a combination of stamping with an elastomeric stamp and an alkanethiol ink followed by chemical etching, *Appl. Phys. Lett.*, 64 (1993) 2002–2004; A. Kumar, H. A. Biebuyck, and G. M. Whitesides, Patterning self-assembled monolayers: applications in material science, *Langmuir*, 10 (1994) 1498–1511. The pattern of photoresist consisted of an array of 20 parallel lines, 20 μm thick, 50 μm wide, and separated by 50 μm. The lines of photoresist were ~2.5 cm long, and connected to a 4×4 mm² pad at each end: the pads defined outlines for reservoirs to which fluids could be added. After curing for 1 h at 65° C., the polymer was removed from the master to give a free-standing PDMS mold with an array of microchannels embossed on its surface: this array serves as a diffraction grating. Reservoirs for liquids were cut out through the thickness of the PDMS slab.

The choice of the critical dimensions (depth and width) of the microchannels requires comment. The depth of the channels is determined by the thickness of the photoresist on the master: this thickness can be controlled by adjusting the speed of spin-coating of the photoresist in the photolithographic step. We used Shipley 1110 photoresist coated at 1500 rpm to produce films 20 μm thick; using different spin speeds and photoresists, channels ranging in thickness from 1 μm to 1000 μm could be produced easily. (To make devices with channels thicker than 20 μm, different photoresists have to be employed, e.g., SU-8 50 and SU-8 250 (Microlithography Chemical Corp.).) The width of the microchannels is determined by the mask used in photolithography: we used a high resolution transparency as a mask that places a lower bound of 20 μm on the width of the lines. D. Qin, Y. Xia, and G. M. Whitesides, Rapid prototyping of complex structures with feature sizes larger than 20 μm, *Adv. Mat.*, 8 (1996) 917–919. By using commercial chrome masks, however, microchannels with widths and separations as small as 1 μm can be fabricated. We chose to fabricate devices with relatively wide channels (50 μm) because the production of transparencies is much cheaper and faster than that of chrome masks, and because it enables faster flow of fluid that reduces the switching time of the device.

To form enclosed microchannels, the microfluidic devices were sealed in the following way. First, the PDMS mold and a glass slide were placed in a plasma oxidation chamber and oxidized for 1 minute. The PDMS structure was then placed on the glass slide with the surface relief in contact with the glass. The conformal contact between the mold and glass resulted in an irreversible seal between the two substrates: the bond between the two substrates was so strong that the PDMS mold could not be peeled from the glass substrate without damaging the elastomer. The irreversible seal is a result of the formation of bridging siloxane bonds (Si—O—Si) between the two substrates that result from a condensation reaction between silanol (SiOH) groups that are present at both surfaces after plasma oxidation. FIG. 1 shows a picture of a PDMS mold, with an array of microchannels defined on its surface inset), sealed against a glass slide.

Diffraction of light by the microchannels was controlled by filling them with different solutions of either inorganic salts or dye. Solutions of sodium chloride (NaCl, EM Science), potassium thiocyanate (KSCN, Aldrich), and Azure A (Aldrich) were prepared in deionized water and thermally equilibrated at room temperature prior to use; solutions of dye were filtered to remove particulates. The ranges of concentrations were as follows: NaCl: 0–20% (w/w); KSCN: 30–55% (w/w); Azure A: 0–100 mM. The index of refraction of the solutions of inorganic salts ($n_f$) was estimated using tabulated data (R. C. Weast, Ed. CRC Handbook of Chemistry and Physics, 66th ed., 1985: the indices of refraction in these tables were measured at 589 nm and 20° C. Our diffraction experiments were performed at 633 nm and at room temperature (~22° C.): the index of refraction in our experiments and the tabulated data may differ by 0.002–0.004. We are concerned, however, with differences in phase rather than absolute values of phase so small errors in $n_f$ do not effect greatly the interpretation of our data.): $n_f$ ranges from 1.333 to 1.386 for the NaCl solutions, and from 1.393 to 1.452 for the KSCN solutions. The microchannels were filled by placing a drop of fluid in one reservoir and pulling vacuum from the other end of the microchannels. The microchannels were emptied by applying vacuum and were thoroughly rinsed with deionized water between measurements.

Characterization of the devices as diffraction gratings was performed with a He—Ne laser (633 nm). The incoming laser beam was centered on the array of microchannels, and the intensity of the diffracted beams was recorded using a photodiode (Newport, Model 818-SL) and a power meter (Newport, Model 1830-C) positioned ~2 m from the grating: this distance allowed spatial resolution of the diffracted beams. The diameter of the laser beam at the grating was ~1 mm: approximately 10 microchannels (FIG. 1) and a volume of liquid of ~8 nL were sampled in the diffraction experiments. Specifically, FIG. 1 shows a microfluidic diffraction grating. A PDMS mold containing an array of 20 parallel microchannels (50 μm wide, 20 μm deep, spaced by 50 μm) was sealed against a glass substrate. A dye was pumped through the channels from the reservoirs to provide contrast. The inset shows a magnified image of the channels; the width of this array is ~2 mm. In the diffraction experiments, the diameter of the laser beam at the grating was ~1 mm: approximately 10 microchannels and a volume of liquid of 8 nL were therefore sampled.

Figure 8:
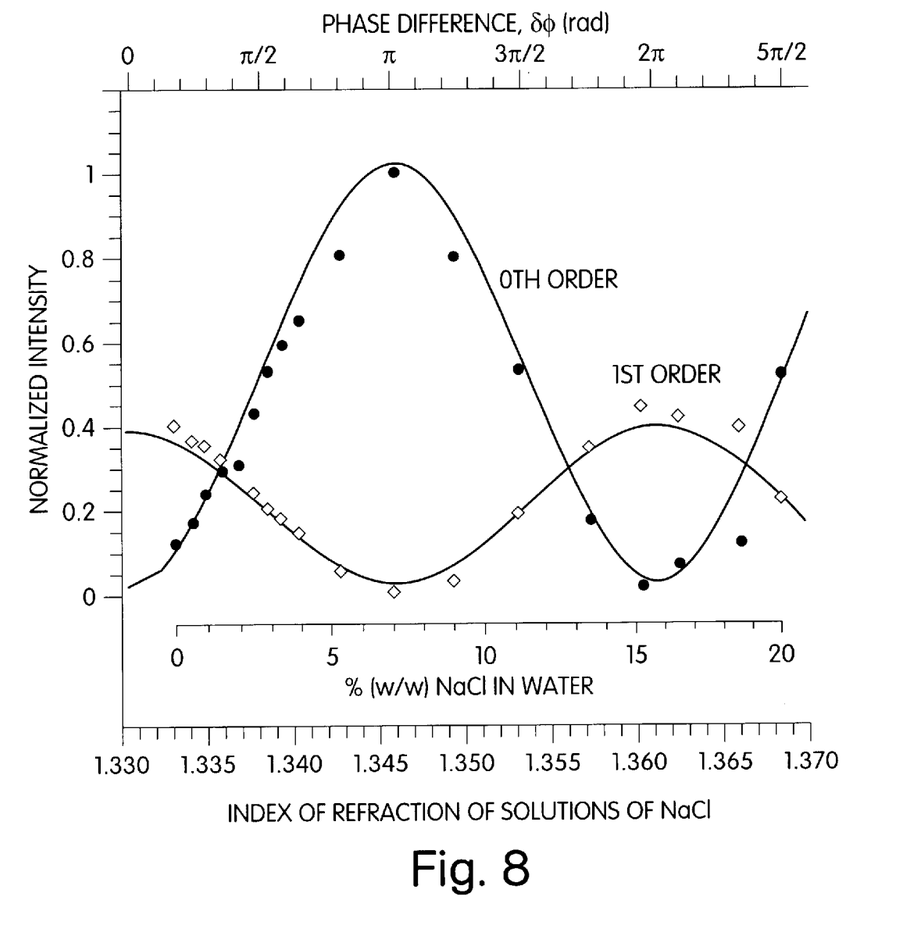
FIG. 8 shows variation in intensities of the 0th and 1st order beams of the diffraction pattern from a microfluidic grating of FIGS. 1–3 as a function of concentration of NaCl in solutions filling the microchannels.

We investigated the influence of the index of refraction of a solution on the diffraction pattern generated by the microfluidic device. The intensities of 0th and 1st order beams of the diffraction pattern from an array of microfluidic channels filled with solutions of NaCl are plotted in FIG. 8 as a function of the concentration of salt (The diffraction pattern of the empty PDMS grating remained constant throughout the experiments, indicating that the PDMS was not swelled by aqueous solutions.). The insertion loss of ~0.1 dB shows that absorption and reflection by PDMS and glass have a small effect on the performance of the device. These data show a modulation of the diffraction when the concentration of NaCl increases. The changes in intensity of the 0th and 1st diffracted orders are large, i.e., ~20 db; this depth of modulation compares favorably to that (16 dB) of an electrostatically actuated diffraction grating that was micromachined in silicon. The solid lines in FIG. 8 represent a fit to these data using the plots generated in FIGS. 6 and 7 and assuming zero absorption. The good agreement between theory and experiment indicates that the modulation of the diffraction pattern is consistent with changes in the phase as the index of refraction of the liquid in the microchannels was varied, i.e., the device operated as a phase grating. The overall modulation was 1.1–1.2 cycles (i.e., 2.3π in phase angle) for NaCl solutions varying from 0–20% (w/w).

A similar experiment was carried out using aqueous solutions of KSCN. In this case, index-matching of PDMS was achieved when the microchannels were filled with a solution containing ~38% (w/w) KSCN: this solution has an index of refraction of ~1.41 (Weast, above).

Figure 9:
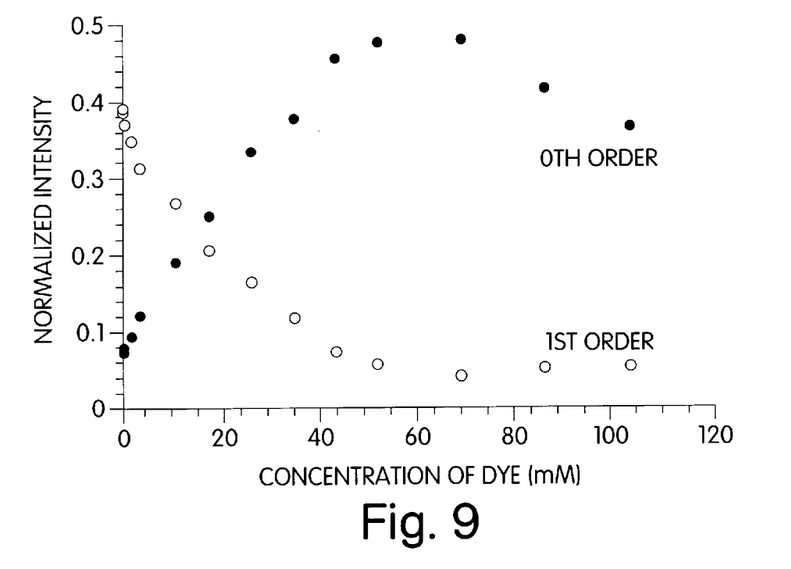
FIG. 9 shows variation in the intensities of the 0th and 1st order of the diffraction pattern from a microfluidic grating of FIGS. 1–3 as a function of the concentration of Azure A in aqueous solutions.
Figure 10:
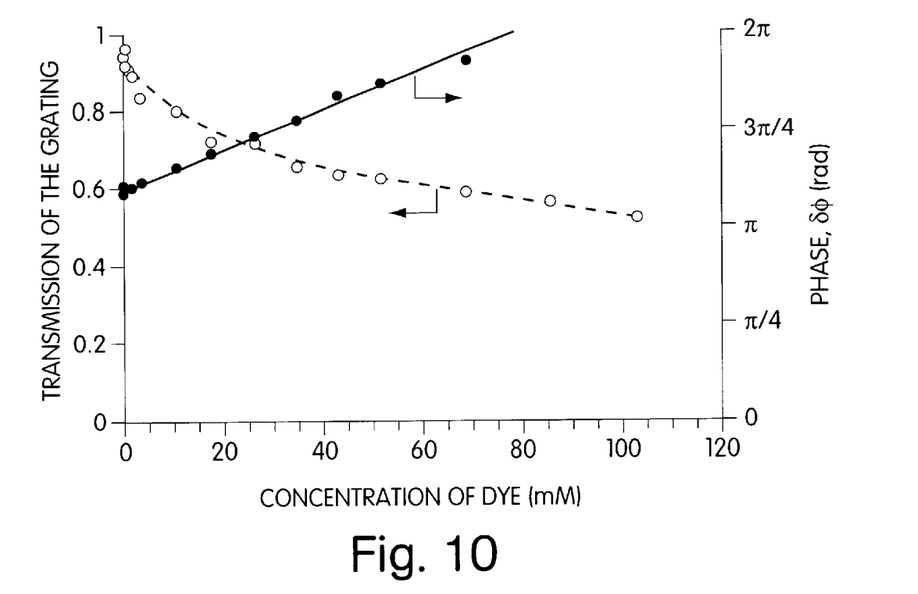
FIG. 10 shows variation of transmission of the device of FIGS. 1–3 (open circles) and phase (closed circles) as a function of concentration of Azure A.

The influence of absorption on the diffraction pattern generated by the microfluidic device was investigated by filling the microchannels with aqueous solutions of a dye, Azure A, that has a maximum in absorption ($\epsilon$~$10^5$ $M^{-1}$ $cm^{-1}$) at 633 nm. The variations in the intensities of the 0th and 1st order beams of the diffraction pattern as a function of the concentration of dye are shown in FIGS. 9 and 10. FIG. 9 shows that the modulation of the intensity of the diffracted beams was only partial: neither the 0th nor the 1st order diffracted beams became totally illuminated or extinct as the concentration of dye was changed. This behavior is consistent with differences between both the amplitude and phase of the light passing through PDMS and the fluid in the microchannels FIGS. 6 and 7.

Both the absorption and the phase of the light passing through the diffraction grating can be determined simultaneously. FIG. 10 shows the variation of the transmission of the device, determined by summing the intensity of the first six diffracted orders (0 to ±5), as a function of concentration. As expected, the transmission decreased as the concentration of dye in solution was increased but, since the microchannels that contain the absorbing fluid represent only half of the surface area of the grating, the lower value of transmission of the device was only 0.5. The phase can be determined from the relative intensity of the 0th and 1st order diffracted beams, the measured transmittance of each solution, and the calculated plots shown in FIGS. 6 and 7: the phase determined for each solution is shown in FIG. 10. The phase increases linearly with the concentration of dye in solution.

The results presented in this section indicate that this optical microfluidic device could be used to monitor changes in the index of refraction and absorption of a fluid. This device could potentially be useful in applications that require dynamic, real-time monitoring of the evolution of the properties of a liquid, for example, during chemical reactions in μTAS. In the device presented here, for a laser beam diameter of ~1 mm, a volume of liquid of 8 nL was sampled: this volume approaches those encountered in μTAS. This grating is amenable to several methods of pumping the liquids through the microchannels that would provide time resolution during a dynamic measurement of the diffraction pattern: application of vacuum and pressure, and electroosmotic pumping.

The switching time of the device is equal to the time it takes for fluid in the volume illuminated by the laser beam to be displaced. Application of vacuum caused the fluid in the 2.5 cm long microchannels to be completely displaced in less than 1 s: this pumping rate therefore results in a switching time of about 50 ms in the region sampled by the laser beam. If the liquids were pumped by pressure or electroosmosis then the switching time would be longer for the experimental conditions common in μTAS: for example, electroosmotic pumping in this device caused by applying an electric field of 500 V/cm across the 20 microchannels would result in a switching time of ~500 ms. FIG. 8 shows variation in the intensities of the 0th (filled circles) and 1st (open diamonds) order beams of the diffraction pattern from a microfluidic grating as a function of the concentration of NaCl in solutions filling the microchannels. The measurements were carried out at 633 nm. The data for the 1st order beams are an average of the positive and negative beams; both sets of data were normalized to the total intensity of light transmitted through the device. A second x-axis is labeled that shows the index of refraction of the solutions determined from tabulated values (Weast, R. C., above). The index of refraction varies linearly with concentration from 1.333 for pure water to 1.3684 for a 20% NaCl solution: this difference in index of refraction corresponds to ~1.1 cycle of modulation (Eq. 2). The solid lines show the variation of the intensities of the 0th and 1st orders for a pure phase grating as a function of the phase difference (top x-axis) calculated from Eq. 1. The change in phase over the range of concentrations determined from the fit is ~2.3π, i.e., ~1.2 cycles of modulation. The modulation of the microfluidic diffraction grating is therefore consistent with a change in phase induced by a variation solely in the index of refraction of the fluid filling the microchannels. The deviation in the experimental data from the fits probably arises from instabilities in the He—Ne laser and detector that result in errors of ±5% in the measurements.

FIG. 9 shows variation in the intensities of the 0th (closed circles) and 1st (open circles) orders of the diffraction pattern from a microfluidic grating as a function of the concentration of Azure A in aqueous solutions. FIG. 10 shows variation of transmission of the microfluidic device (open circles) and phase (closed circles) as a function of concentration of Azure A. The phase was determined from fits to Eq. 1 of the diffraction pattern for each solution of dye; the solid line through these data represent a linear fit. The dotted line is a guide to the eye for the transmission of the device. The transmittance of the liquid in the channels was fitted to the Beer-Lambert law (not shown). The low value of $\epsilon d$ (~11 M) produced by this fit compared to the value estimated from the coefficient of extinction of Azure A and the thickness of the microchannels ($\epsilon d$=200 M) can be explained by the deviation from the ideal behavior described by the Beer-Lambert law at high concentrations (>10 mM) of an absorbing species.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A method comprising:
   joining a pre-oxidized elastomeric surface to a second pre-oxidized surface, wherein the elastomeric surface and the second surface form an irreversible liquid-impermeable seal therebetween in a microfluidic structure.

2. A method as in claim 1, comprising joining the elastomeric surface and the second surface to form an irreversible liquid-impermeable seal therebetween in the absence of auxiliary adhesive.

3. A method as in claim 1, further comprising pre-oxidizing the elastomeric surface and the second surface by exposing the elastomeric surface and the second surface to plasma.

4. A method as in claim 1, wherein the joining step comprises joining first portions of the elastomeric surface to the second surface while leaving a second portion of the elastomeric surface, intervening the first portions of the elastomeric surface, free of contact with the second surface.

5. A method as in claim 1, the joining step comprising contacting first portions of the second surface with the elastomeric surface while leaving a second portion of the second surface, intervening the first portions of the second surface, free of contact with the elastomeric surface.

6. A method as in claim 1, wherein the second surface is polymeric.

7. A method as in claim 1, wherein the second surface is metal.

8. A method comprising:
applying an elastomeric surface to a second surface in the absence of auxiliary adhesive and at a temperature of between about 16° C. and about 27° C., wherein the elastomeric surface and the second surface bond to form an irreversible liquid-impermeable seal therebetween in a microfluidic structure.

9. A method as in claim 8, further comprising pre-oxidizing the elastomeric surface and the second surface prior to the applying step.

10. A method as in claim 8, further comprising exposing the elastomeric surface and the second surface to plasma prior to the applying step.

11. A method as in claim 8, wherein the second surface is polymeric.

12. A method as in claim 8, the applying step comprising contacting first portions of the elastomeric surface with the second surface while leaving a second portion of the elastomeric surface, intervening the first portions of the elastomeric surface, free of contact with the second surface.

13. A method as in claim 8, the applying step comprising contacting first portions on the second surface with the elastomeric surface while leaving a second portion of the second surface, intervening the first portions of the second surface, free of contact with the elastomeric surface.

14. A method as in claim 8, wherein the second surface is metal.

15. A method comprising:
joining a pre-oxidized elastomeric surface, comprising at least one microchannel formed in the elastomeric surface, to a second pre-oxidized surface, wherein the elastomeric surface and the second surface form an irreversible liquid-impermeable seal therebetween.

16. The method of claim 1, wherein the elastomeric surface comprises at least one microchannel.

17. The method of claim 1, comprising joining the elastomeric surface to the second pre-oxidized surface in the absence of auxiliary adhesive.

18. The method of claim 1, comprising joining the elastomeric surface to the second pre-oxidized surface at a temperature of between about 16° C. and about 27° C.

19. The method of claim 8, wherein the elastomeric surface comprises at least one microchannel.

20. The method of claim 8, wherein the temperature is between 18° C. and about 23° C.

21. The method of claim 15, comprising joining the elastomeric surface to the second pre-oxidized surface at a temperature of between about 16° and about 27° C.

22. The method of claim 15, wherein the temperature is between about 18° C. and about 23° C.

23. The method of claim 15, further comprising pre-oxidizing the elastomeric surface and the second surface by exposing the elastomeric surface and the second surface to plasma.

24. A method as in claim 15, wherein the joining step comprises joining first portions of the elastomeric surface to the second surface while leaving a second portion of the elastomeric surface, interverning the first portions of the elastomeric surface, free of contact with the second surface.

25. A method as in claim 15, the joining step comprising contact first portions of the second surface with the elastomeric surface while leaving a second portion of the second surface, intervening the first portions of the second surface, free of contact with the elastomeric surface.

26. A method as in claim 15, wherein the second surface is polymeric.

27. A method as in claim 15, wherein the second surface is metal.

* * * * *